United States Patent [19]
DiFrancesco et al.

[11] Patent Number: 5,849,021
[45] Date of Patent: Dec. 15, 1998

[54] ELONGATED THUMB LOOP FOR SURGICAL INSTRUMENT

[75] Inventors: Francis J. DiFrancesco, Foxboro, Mass.; Clive B. Reay-Young, Harrogate, United Kingdom

[73] Assignee: TNCO, Inc., Whitman, Mass.

[21] Appl. No.: 843,556

[22] Filed: Apr. 18, 1997

[51] Int. Cl.⁶ .................................................. A61B 17/32
[52] U.S. Cl. ......................... 606/174; 606/170; 606/205
[58] Field of Search ..................... 606/170, 174, 606/205

[56] References Cited

U.S. PATENT DOCUMENTS

| 5,499,992 | 3/1996 | Meade et al. | 606/174 |
| 5,611,813 | 3/1997 | Lichtman | 606/174 |

*Primary Examiner*—Michael Buiz
*Assistant Examiner*—Julian W. Woo
*Attorney, Agent, or Firm*—Stephen Y. Chow, Esq.

[57] ABSTRACT

A handle for endoscopic surgical instruments with an elongated thumb loop optimized for providing support and driving force in endoscopic surgery.

8 Claims, 2 Drawing Sheets

ELONGATED THUMB LOOP FOR SURGICAL INSTRUMENT

BACKGROUND OF THE INVENTION

The field of the invention is that of micro-instrumentation, that is, articulating, hand-held, instruments used in microsurgery and like applications, for cutting or punching out tissue. The invention is particularly advantageous for use with such instrumentation.

FIG. 1 shows a typical endoscopic instrument with tubular extension 30 of 4–10 inches long and 3–5 mm in diameter connecting an effector tip assembly 40, which may be a grasper, a punch, a cutter or some combination, with a stationary handle 10 and an actuating handle 20. Typically, the stationary handle provides a thumb loop 15 angled downward from a portion 17 in which the tubular extension 30. Fitting portion 17 provides for a pivot 18 for actuating handle 20 and houses a linkage to manipulate effector 40 by movement of actuator handle 20. The instrument is manipulated with the operator's thumb in the thumb loop and one or more other fingers moving the actuator handle. In the prior art, the thumb loop 15 is generally of a circular or elliptical shape of a size adapted for a thumb to engage at a generally perpendicular angle.

SUMMARY OF THE INVENTION

Objectives of the present invention include the provision of an improved thumb loop, for use with an endoscopic instrument, that provides optimal comfort to operators with diverse thicknesses of their thumbs engaging the loop at a variety of angles and allowing such operators to support and manipulate tubular extension 30 and effector tip 40 optimally. The invention includes a handle, for grasping by a human thumb, angled downward from a fitting portion wherein the inside radius of the top portion of the thumb loop is smaller than the inside radius of the bottom portion of the thumb loop, defining a pear-shaped inner surface of the loop. An advantage of the invention is to allow the operator to move the effector assembly firmly along the axis of the effector assembly (with or without the extension), for example, through tissue inside a patient, with the operator's thumb firmly braced along a portion of the pear-shaped surface conforming in width to the operator's thumb.

The elongated loop also allows for comfortable "palming" of the instrument where the palm engages the outside portion of the loop and the fingers engage the other handle. This use allows the greater exertion of forward force using the palm rather than just the thumb.

DETAILED DESCRIPTION

Figure 1:
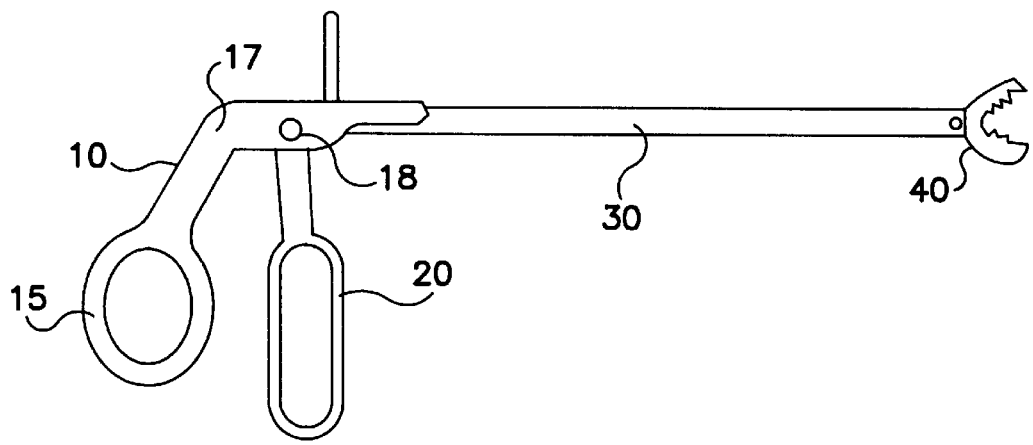
FIG. 1 shows a typical endoscopic surgical instrument with a prior art thumb loop.
Figure 2:
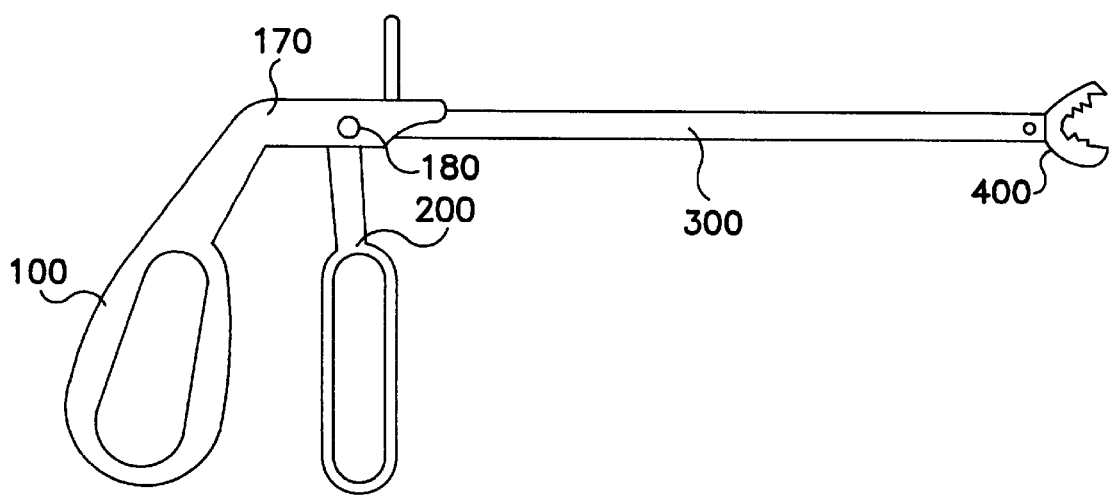
FIG. 2 shows the elongated thumb loop of the invention as part of an endoscopic surgical instrument.
Figure 3:
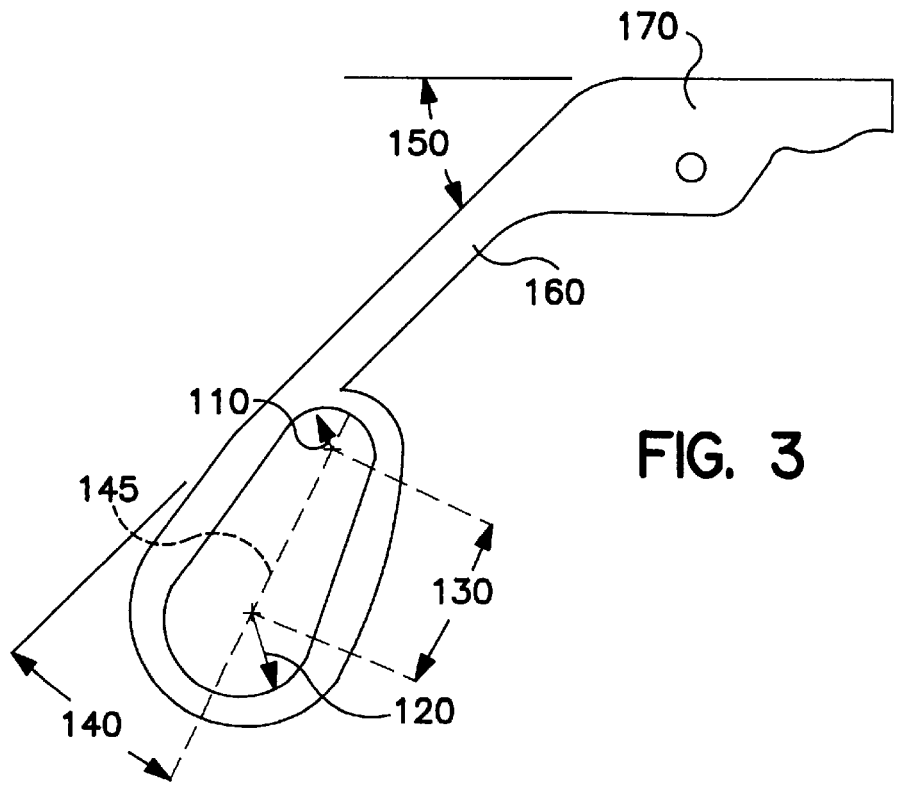
FIG. 3 shows details of the handle with the elongated thumb loop of the invention.
Figure 3A:
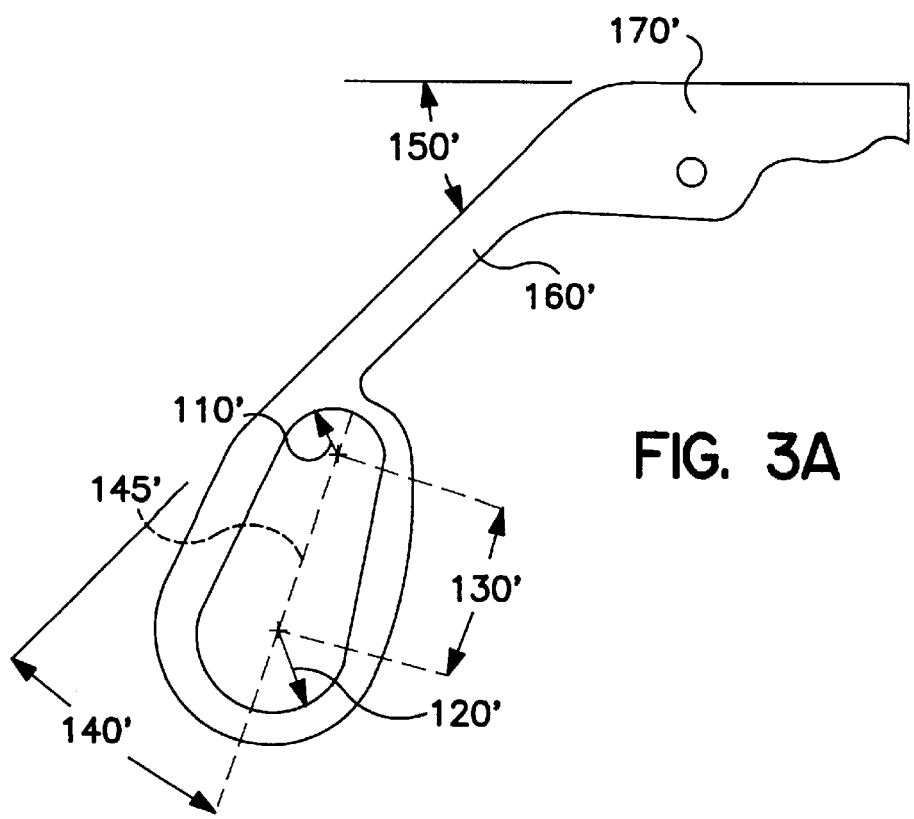
FIG. 3A shows details of alternative elongated thumb loop as an alternative embodiment of the invention.

FIG. 2 shows an endoscopic instrument with the elongated thumb loop 100. FIG. 3 shows details of the handle for an endoscopic instrument with a preferred embodiment of the thumb loop 100. In this embodiment, shank 160 is angled approximately 45° downwards 150 from the axis of fitting portion 170. Thumb loop 100 is attached to shank 160 at a position distal from the fitting portion 170 and further angled approximately 19° downwards 140 from the shank 160 to the centerline or axis 145 of the loop. The inner radius 110 of the top portion of the loop is approximately 0.250 inches, and inner radius 120 of the bottom portion of the loop is approximately 0.425 inches, with a separation 130 of their centers of approximately 0.945 inches, thereby forming a pear-shaped inner surface. It has been found that operators with diverse thicknesses of their thumbs can operate an endoscopic instrument with this thumb loop 100 comfortably and optimally with their thumbs engaging the inside surface of loop 100 at various angles in a region corresponding to the thickness of their thumbs. Shank 160 and its extension by the outside surface of loop 100 provide a convenient surface for comfortably "palming" the instrument.

FIG. 3 shows a handle for an endoscopic instrument with an alternative embodiment of the thumb loop 100'. In this embodiment, shank 160 is again angled approximately 45° downwards 150 from the axis of fitting portion 170. Thumb loop 100' is attached to shank 160 further angled approximately 26° downwards 140' from the shank 160 to the loop axis 145'. The inner radius 110' of the top portion of the loop is approximately 0.175 inches, and inner radius 120' of the bottom portion of the loop is approximately 0.400 inches, with a separation 130' of their centers of approximately 0.925 inches.

It should be understood that some of the stated dimensions may be varied without losing the advantage of the invention, and the loop may be part of a movable handle, rather than a handle stationary relative to the tubular extension. Other configurations are possible, with the advantage that the operator's thumb is firmly braced against the narrowest portion of a pear-shaped inner surface of the thumb loop when exerting force along the axis of the effector, that is, the narrowest end of the pear-shaped inner surface is in the direction of the exertion of force.

What is claimed is:

1. A handle for supporting and effecting motion of an effector fitted to said handle along an axis, said handle comprising:

(a) a fitting portion for fitting said effector and defining said axis; and (b) an elongated thumb loop for engaging a human thumb connected to said fitting portion at an acute angle from said axis and defining an inner cross section having an arcuate end of a first inner radius proximal to said axis, an arcuate opposite end of a second inner radius distal said axis, said second inner radius larger than said first inner radius, and having two substantially straight sides each tangentially connecting said arcuate ends on opposite sides.

2. The handle of claim 1 wherein said first inner radius is in the range of approximately 0.175 inches to approximately 0.250 inches and said second inner radius is in the range of approximately 0.400 inches to approximately 0.4250 inches.

3. The handle of claim 2 wherein the center of said first radius is separated from the center of said second radius by a distance of between approximately 0.925 inches and approximately 0.945 inches.

4. The handle of claim 1 wherein said thumb loop is connected to said fitting portion by a shank.

5. The handle of claim 4 wherein said shank forms an acute angle with said axis.

6. The handle of claim 5 wherein said angle is approximately 45°.

7. The handle of claim 6 wherein a loop axis connecting the centers of said first inner radius and said second inner radius forms an angle with said shank of between approximately 19° and approximately 26°.

8. A handle for supporting and effecting motion of an effector fitted to said handle along an axis, said handle comprising:
   (a) a fitting portion for fitting said effector and defining said axis;
   (b) a shank connected to said fitting portion directed distally to said effector at an approximately 45° angle from said axis; and
   (c) a thumb loop connected to said shank further distal to said effector and defining a pear-shaped inner cross section having an arcuate end of a first inner radius proximal to said axis, an arcuate opposite end of a second inner radius distal said axis, said second inner radius larger than said first inner radius, and having two substantially straight sides each tangentially connecting said arcuate ends on opposite sides, said cross-section having an axis disposed to said shank at an angle from approximately 19° to approximately 26° further from said axis and with a first inner radius proximal said shank of approximately 0.175 inches to approximately 0.250 inches and a second inner radius distal said shank of approximately 0.400 inches to approximately 0.4250 inches, said first and second inner radii separated at their centers by a distance of between approximately 0.925 inches and approximately 0.945 inches.

* * * * *